United States Patent [19]

Fukuda

[11] Patent Number: 4,781,197
[45] Date of Patent: Nov. 1, 1988

[54] CLIP TYPE ELECTRODE FOR ELECTROCARDIOGRAPHS

[75] Inventor: Takashi Fukuda, Tokyo, Japan

[73] Assignee: Fukuda Denshi Co., Ltd., Tokyo, Japan

[21] Appl. No.: 867,593

[22] Filed: May 27, 1986

Related U.S. Application Data

[63] Continuation of Ser. No. 644,908, Aug. 28, 1984, abandoned.

[30] Foreign Application Priority Data

Apr. 12, 1984 [JP] Japan ............................ 59-54010[U]

[51] Int. Cl.$^4$ ................................................ A61B 5/04
[52] U.S. Cl. ...................................... 128/644; 128/802
[58] Field of Search ............... 128/639, 644, 642, 346, 128/802

[56] References Cited

U.S. PATENT DOCUMENTS

| | | | |
|---|---|---|---|
| 1,640,061 | 8/1927 | Wappler | 128/802 |
| 1,644,803 | 10/1927 | Wappler | 128/802 |
| 2,611,368 | 9/1952 | Pecora | 128/639 |
| 2,782,786 | 2/1957 | Krasno | 128/639 |
| 2,831,174 | 4/1958 | Hilmo | 128/639 X |
| 3,067,749 | 12/1962 | Walters | 128/639 |
| 3,323,516 | 6/1967 | Salter | 128/644 |
| 4,112,951 | 9/1978 | Hulka et al. | 128/346 |
| 4,337,774 | 7/1982 | Perlin | 128/346 X |
| 4,484,581 | 11/1984 | Martin et al. | 128/346 |

FOREIGN PATENT DOCUMENTS

| | | | |
|---|---|---|---|
| 0204616 | 12/1983 | Fed. Rep. of Germany | 128/644 |
| 2133884 | 8/1984 | United Kingdom | 128/644 |

Primary Examiner—Kyle L. Howell
Assistant Examiner—Angela D. Sykes
Attorney, Agent, or Firm—Armstrong, Nikaido, Marmelstein & Kubovcik

[57] ABSTRACT

A clip-type electrode for an electrocardiograph includes a pair of clamping plates for being opened and closed relative to each other about a common shaft and having concave surfaces facing each other, an electrode member mounted on one of the clamping plates, and a leaf spring bent into a U-shaped configuration for biasing ends of the clamping plates remote from the common shaft towards each other. Each of the pair of clamping plates has a slot at a position adjacent to the shaft for accommodating the leaf spring passed therethrough, and a plurality of grooves formed in an outer surface thereof and spaced at successively greater distances from the shaft. One end of the leaf spring is fitted into a one of the plurality of grooves in one of the clamping plates, and the other end of the leaf spring is fitted into one of the plurality of grooves in the other of the clamping plates, the grooves being chosen based upon the thickness of a limb, such as the wrist or ankle of a human body, that is to have the clip-type electrode attached thereto. The limb can thus be clamped with a prescribed clamping force irrespective of the thickness of the limb.

2 Claims, 3 Drawing Sheets

CLIP TYPE ELECTRODE FOR ELECTROCARDIOGRAPHS

This application is a continuation of application Ser. No. 644,908, filed Aug. 28, 1984, now abandoned.

BACKGROUND OF THE INVENTION

This invention relates to an electrode used in an electronic instrument, such as an electrocardiograph, adapted to measure the state of a living body, and more particularly to a clip-type electrode used in an electrocardiograph.

An electrocardiograph is widely utilized to diagnose the heart of a human or other living body. In operation, a minute electric current induced in the surface of the skin of, e.g., the human body, is applied to an electrocardiograph composed of electronic circuitry external to the body. The electrocardiograph measures and observes changes in electrical potential caused by changes in the minute current ascribable to the heartbeat. Based on the results of such analysis, the doctor can make a diagnosis on whether or not the patient's heart is functioning normally.

FIG. 1 shows a system for measuring changes in electrical potential by using an electrocardiograph. In the drawing, numeral 1 designates an electrocardiograph composed of electronic circuitry. A lead 2 is connected from the electrocardiograph 1 to an electrical distributor 3 from which four leads $4_1$, $4_2$, $4_3$, and $4_4$ are connected to one end of respective clip-type electrodes $5_1$, $5_2$, $5_3$ and $5_4$ clipped to the wrists and ankles of a patient lying lengthwise on a bed, not shown. The other ends of the clip-type electrodes $5_1$, $5_2$, $5_3$ and $5_4$ are respectively connected to leads $6_1$, $6_2$, $6_3$ and $6_4$ and thence to a display unit 7 such as a CRT.

In the above-described system, changes in the electrical potential induced in the wrists and ankles of the human body are sensed by the clip-type electrodes $5_1$, $5_2$, $5_3$ and $5_4$ and displayed by the display unit 7. Based on the voltage waveform on the display unit, the doctor may make a diagnosis on whether the heart function is normal or abnormal.

In the foregoing system, the wrists and ankles to which the clip-type electrodes $5_1$, $5_2$, $5_3$ and $5_4$ are attached are not truly cylindrical in shape and differ in thickness from one patient to another. The thickness also differs with one and the same patient depending on the positions at which the electrodes $5_1$ to $5_4$ are attached.

FIG. 2 shows the construction of a prior-art clip-type electrode. As shown, the electrode 5' comprises a pair of curved clamping plates 8, 8' adapted to be clipped on limb such as a wrist or ankle. These plates 8, 8' are biased by a spring 5b disposed on a shaft 5a so that the ends of the plates are caused to approach each other. An electrode plate 9 is affixed to the inner surface of the clamping plate 8 by a fastener such as nut. A pair of terminals 10, 10' provided on the outside of the clamping plate 8 are connected to the electrode plate 9.

The above described clip-type electrode 5' is manually grasped at the rear part of the clamping plates 8, 8' so that the forward parts of the clamping plates 8, 8' are opened by pivoting about the shaft 5a for attachment to a limb such as the wrist or ankle of the human body.

As mentioned above, the wrist or ankle of the human body has a cross-sectional configuration and thickness that differ from one individual to another. When a wrist or ankle is clamped by the clamping plates 8, 8', no particular problem is encountered if the wrist or ankle of the individual has a thickness which enables the spring 5b to apply a clamping force of appropriate strength. Where the wrist or ankle has a thickness that causes the spring 5b to apply an excessive clamping force or a clamping force which is too weak, various disadvantages result, one of which is pain or discomfort experienced by the individual. If the individual has a wrist or ankle which is particularly stout, moreover, the limb cannot be passed through the clearance between the ends of the clamping plates 8, 8' even when the clamping plates are spread widely apart. This makes it impossible to attach the electrode to the limb.

SUMMARY OF THE INVENTION

An object of the present invention is to provide a clip-type electrode free of the abovementioned disadvantages encountered in the prior art.

Briefly, the present invention provides a clip-type electrode for an electrocardiograph comprising a pair of clamping plates adapted for being opened and closed about a common shaft and having concave surfaces facing each other, an electrode member mounted on one of the clamping plates, and a leaf spring bent into a U-shaped configuration for biasing ends of the clamping plates remote from the common shaft towards each other. Each of the pair of clamping plates has a slot at a position adjacent to the shaft for accommodating the leaf spring passed therethrough, and a plurality of grooves formed in an outer surface thereof and spaced at successively greater distances from the shaft. One end of the leaf spring is fitted into a one of the plurality of grooves in one of the clamping plates, and the other end of the leaf spring is fitted into one of the plurality of grooves in the other of the clamping plates, the grooves being chosen based upon the thickness of a limb, such as the wrist or ankle of a human body, that is to have the clip-type electrode attached thereto. A limb can thus be clamped with an optimum clamping force selected depending upon the thickness of the limb.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 1:
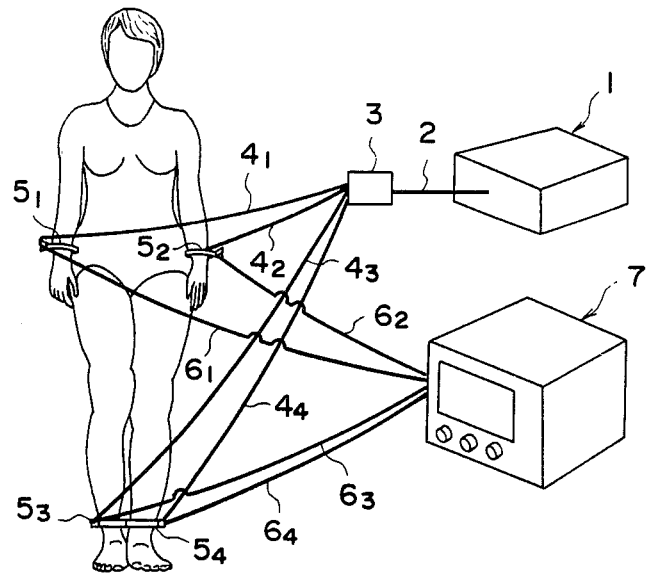
FIG. 1 is a schematic view showing a system for measuring changes in the electrical potential of a human body with the aid of an electrocardiograph.
Figure 2:
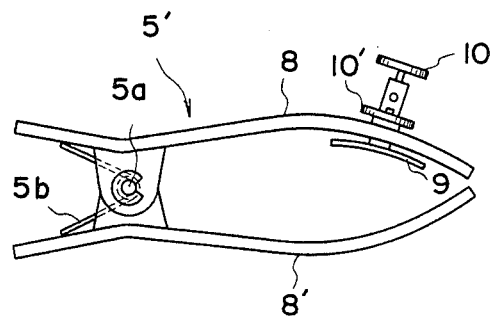
FIG. 2 is a side view showing the construction of the prior-art clip-type electrode.
Figure 3:
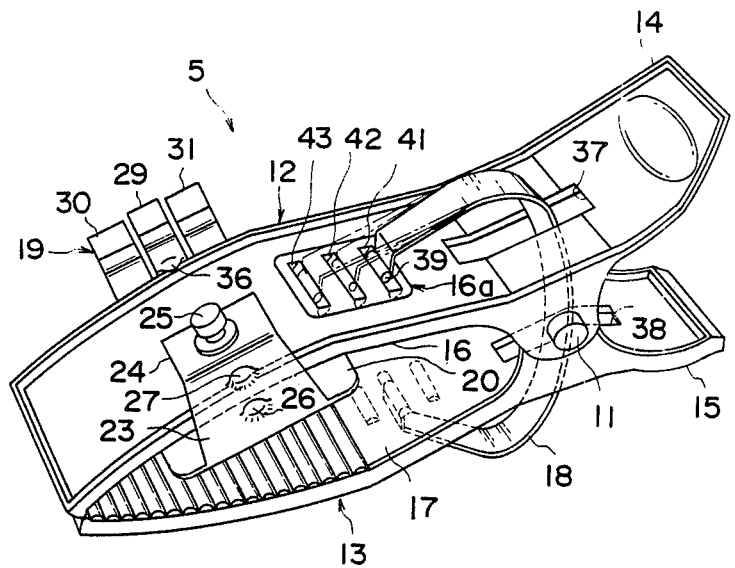
FIG. 3 is a perspective view showing the construction of the clip-type electrode according to the present invention.
Figure 4:
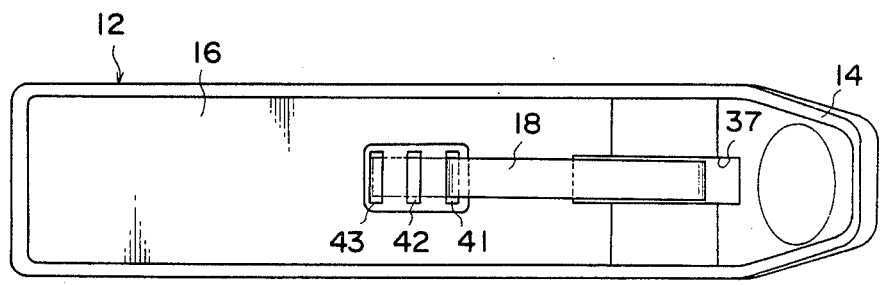
FIG. 4 is a plan view illustrating the clip-type electrode of FIG. 3.
Figure 5:
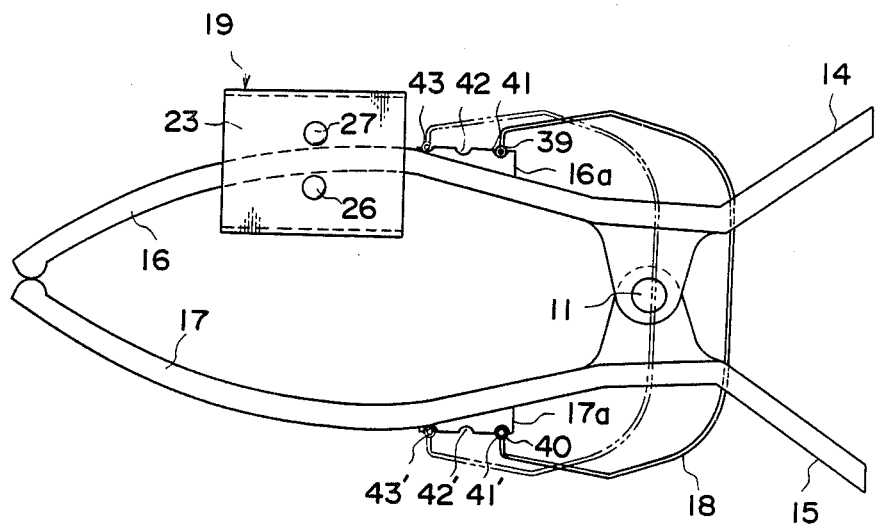
FIG. 5 is a side view showing the manner in which the clip-type electrode of FIG. 3 is used.
Figure 6:
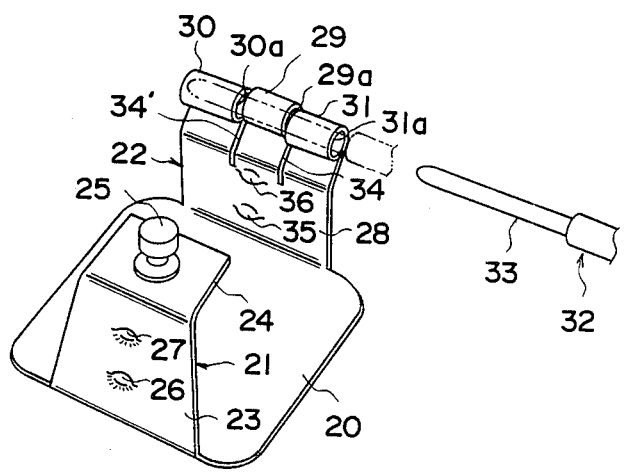
FIG. 6 is a perspective view showing the construction of an electrode member.

FIG. 3 shows an embodiment of a clip-type electrode according to the present invention. FIGS. 4 and 5 show the same clip-type electrode in plan and side views, respectively, and FIG. 6 is a perspective view showing the construction of the electrode member or electrode proper. The clip-type electrode 5 is constructed of a pair of curved clamping plates 12, 13 that may be turned relative to each other about a shaft 11. Rearwardly of the shaft 11, the plates 12, 13 are formed as outwardly bent grasping sections 14, 15. Grasping the sections 14, 15 causes the distal ends of the clamping plates 12, 13 remote from the shaft 11 to spread apart about the shaft. Forwardly of the shaft 11, the clamping plates 12, 13 are formed as curved clamping sections 16, 17 presenting concave surfaces facing each other. These clamping sections 16, 17 clamp the limb of a living body, such as a wrist or ankle of the human body. Formed in the clamping plates 12, 13 adjacent to the shaft 11 are slender, elongate slots 37, 38, respectively, of a rectangular configuration. Projections 16a, 17a each having a flat upper face are formed on the outer surface of the clamping sections 16, 17 adjacent to the slots 37, 38, respectively. The projection 16a is formed to include a plurality (three in the illustrated embodiment) of engagement grooves 41, 42, 43 spaced at successively greater distances from the shaft 11. Likewise, the projection 17a is formed to include a plurality (three) of engagement grooves 41', 42', 43' spaced at successively greater distances from the shaft 11. As will be described in detail below, the grooves 41-43, 41'-43' serve to engage the ends 39, 40 of a leaf spring 18 which passes through the slots 37, 38.

The leaf spring 18 consists of a metal strip bent into a U-shaped configuration, both ends 39, 40 of the leaf spring being curled into a shape that will allow them to be fitted into selected ones of the grooves 41-43, 41'-43', respectively. Specifically, the leaf spring 18, upon being passed through the slots 37, 38, has its curled end portions 39, 40 spread outwardly against the restoring force of the spring and inserted into prescribed ones of the grooves 41-43, 41'-43', respectively. Owing to the restoring force of the leaf spring 18, the ends 39, 40 thereof urge the clamping plates 12, 13 toward each other so that the distal ends thereof remote from the shaft 11 are brought together. When one grasps and applies pressure to the grasping sections 14, 15 of the respective clamping plates 12, 13, the latter turn about the shaft 11 so that their distal ends spread apart. By inserting the limb of the living body between the spread clamping sections 16, 17 and then releasing the grasping sections 14, 15, the clamping sections 16, 17 will clamp the assembly to the limb. At this time the ends 39, 40 of the leaf spring 18 are fitted into proper ones of the slots 41-43, 41'-43', respectively, the particular slots being selected depending upon the thickness of the limb. This enables the leaf spring 18 to apply a clamping force of a suitable strength to the clamping plates 12, 13.

An electrode member 19 for providing external circuitry with an electric potential generated by the living body is attached to the right and left longitudinal edges of the clamping plate 12. The electrode member 19 is formed of resilient, electrically conductive metallic material and, as shown in FIG. 6, comprises a substantially rectangular flat pressing plate section 20 adapted to be pressed against the limb of the living body, and a pair of engagement plates 21, 22 directed upwards from both edges of the plate section 20. Of the two engagement plates 21, 22, the engagement plate 21 comprises an upright plate 23 and a top plate 24 contiguous thereto and bent inwards parallel to the flat pressing plate section 20. A terminal 25 is provided approximately centrally of the top plate 24 and connected to one end of an electrical lead the other end of which is connected to the display unit 7.

The inner surface of the upright plate 23 is formed to include a first boss 26 projecting towards the opposite engagement plate section 22 at a predetermined distance from the flat plate section 20, and a second boss 27 projecting in a similar manner at a predetermined distance from the first boss 26.

The engagement plate 22 comprises an upright plate 28 and trifurcated support parts or tongues 29, 30 and 31 divided from one another by slits 34, 34'. The distal ends of the tongues 29, 30, 31 are curled into tubular insertion openings 29a, 30a, 31a, respectively. The intermediate tongue 29 is biased slightly outwards with respect to the two terminal tongues 30, 31. When an electrode rod 33 is introduced into the tubular insertion openings 29a, 30a and 31a at the distal ends of the tongues 29, 30 and 31, the rod 33 is pressed by the tongue 29 biased in the above described manner so that it can be positively held in the openings 29a, 30a and 31a without the risk of accidental removal. Connected to the end portion of the electrode rod 33 is a conductor the other end whereof is connected to the electrocardiograph.

The inner surface of the upright plate 28 is formed to include first and second bosses 35, 36 at positions opposing the respective bosses 26, 27 provided on the upright plate 23. As shown in FIG. 5, the electrode member 19 is fixedly mounted on the clamping plate 12 with the first bosses 26, 35 and the second bosses 27, 36 holding the left and right longitudinal edges of the clamping plate 12. Alternatively, the electrode member 19 may be mounted on the clamping plate 12 with the latter being held between the first bosses 26, 35 and the surface of the pressing plate 20. The pressing plate 20 is thus capable of tilting about the first bosses 26, 35 or second bosses 27, 36 so as to be brought into intimate contact with the limb of the living body.

The method of using the above-described clip-type electrode 5 will now be described. With the left and right plates 21, 22 of the electrode member 19 shown in FIG. 6 spread slightly apart from each other, the electrode member 19 is mounted on the clamping plate 12 in such a manner that the first bosses 26, 35 and second bosses 27, 36 clamp both side edges of the clamping plate 12. Next, with the central portion of the leaf spring 18 penetrating the slots 37, 38, one end portion 39 of the leaf spring 18 is fitted into one of the engagement grooves 41-43, and the other end portion 40 of the leaf spring 18 is fitted into one of the engagement grooves 41'-43', the particular grooves being selected depending upon the thickness of the limb, such as the wrist or ankle of the human body, that is to be contacted by the electrode. The grasping sections 14, 15 are then gripped and pressed toward each other to spread the foremost ends of the clamping plates 12, 13. If the limb, namely the wrist or ankle, is found to have considerable thickness, the ends 39, 40 of the leaf spring 18 are fitted into the respective grooves 41, 41', which are nearest the shaft 11. If the limb is slender, on the other hand, the ends 39, 40 of the leaf spring 18 are fitted into the respective grooves 43, 43' farthest from the shaft 11. After spreading the clamping plates 12, 13 and selecting the proper grooves from among the grooves 41-43, 41'-43' in the foregoing manner, the clip-type electrode 5 is attached to the limb by inserting the limb between the clamping plates 12, 13 and releasing the grasping sections 14, 15. The electric potential which changes in accordance with the heartbeat of the living body is applied to the display unit by the electrode member 19, thereby allowing the heart to be diagnosed on the basis of the change in electric potential observed as a potential waveform.

As described above, the clip-type electrode for an electrocardiograph according to the present invention includes a pair of clamping plates each having a clamping section the outer surface of which is formed to include a plurality of engagement grooves spaced at successively greater distances from a shaft joining the clamping plates together, and a leaf spring bent into a U-shaped configuration and having distal end portions adapted to be fitted into selected ones of the engagement grooves. This arrangement permits the leaf spring to subject the clamping plates to a clamping force suited to the thickness of the limb to which the electrode is to be attached, thereby assuring that a patient undergoing electrocardiographic diagnosis will experience no discomfort.

In addition, the electrode member can be attached to the clamping plate very easily merely by using the engagement plate sections provided on both sides of the flat pressuring plate section to hold both side edges of the clamping plate.

As many apparently widely different embodiments of the present invention can be made without departing from the spirit and scope thereof, it is to be understood that the invention is not limited to the specific embodiments thereof except as defined in the appended claims.

What I claim is:

1. A clip-type electrode for an electrocardiograph comprising:
    a pair of clamping plates each having a grasping section and a clamping section and being arranged for pivotal movement about a common shaft positioned between said grasping section and said clamping section;
    said clamping sections being curved to have concave surfaces facing each other, and having an electrode member mounted on the clamping section of one of said clamping plates;
    said grasping sections being formed as outwardly bent members such that movement of said grasping sections toward each other causes said clamping plates to pivot about said common shaft to cause said clamping sections thereof to spread apart;
    said clamping plates each having a plurality of engagement grooves formed in the other surfaces of said clamping sections spaced at successively greater distances from said common shaft and having a slot formed through each said grasping section at a position adjacent to said common shaft; and
    a leaf spring means bent into a substantially U-shaped configuration extending through said slots and around said clamping sections and having end portions fitting said engagement grooves, each end portion of said spring means being arranged to removably engage, respectively, a selected one of said engagement grooves on one of said clamping plates for biasing said clamping sections of said clamping plates toward each other;
    said spring means being so arranged that said end portions may be removed from said selected engagement grooves and engaged with other engagement grooves at a different distance from said common shaft so as to adjust clamping force of said clamping plates.

2. A clip-type electrode as recited in claim 1 wherein each clamping section is formed with a projection having a flat face on the outer surface thereof, and said engagement grooves are formed in said flat face.

* * * * *